United States Patent [19]

Shultz et al.

[11] Patent Number: 5,273,906
[45] Date of Patent: Dec. 28, 1993

[54] PROTEIN STAINING COMPOSITIONS AND METHODS

[75] Inventors: John W. Shultz; David L. Leland, both of Verona, Wis.

[73] Assignee: Promega Corporation, Madison, Wis.

[21] Appl. No.: 916,539

[22] Filed: Jul. 20, 1992

Related U.S. Application Data

[62] Division of Ser. No. 615,078, Nov. 19, 1990, Pat. No. 5,132,439.

[51] Int. Cl.$^5$ ............................................. G01N 33/00
[52] U.S. Cl. ........................................ 436/86; 552/106; 552/110; 552/113; 552/114; 552/302; 436/177; 204/180.1; 204/182.8
[58] Field of Search .................. 436/86, 177; 552/106, 552/110, 113, 114, 302, 304; 204/180.1, 182.8

[56] References Cited

U.S. PATENT DOCUMENTS

| | | | |
|---|---|---|---|
| 2,055,607 | 9/1936 | Linch et al. | 552/110 |
| 2,085,736 | 7/1937 | Calcott et al. | 552/113 |
| 4,023,933 | 5/1977 | Bradford et al. | 23/230 B |
| 4,219,337 | 8/1980 | Grossberg et al. | 422/56 X |
| 4,966,854 | 10/1990 | Fleming | 436/86 X |
| 5,013,857 | 5/1991 | Berneth et al. | 552/302 X |
| 5,101,020 | 3/1992 | Fleming | 436/86 X |

FOREIGN PATENT DOCUMENTS 2914299 10/1980 Fed. Rep. of Germany .
159907 1/1964 U.S.S.R. .

OTHER PUBLICATIONS

In re Durden, 226 USPQ 359.
In re Pleuddermann, 15 USPQ 2nd 1738.
H. Schägger et al., "Coomassie Blue-Sodium dodeccyl Sulfate-Polyacrylamide Gel Electrophoresis, for Direct Visualization of Polypeptides during Electrophoresis", Anal. Biochem. 173, 201-205 (1988).
B. D. Hames, "Peptide mapping by Limited Proteolysis Using SDS-Polyacrylamide Gel Electrophoresis", in Gel Electrophoresis of Proteins—a Practical Approach.
B. Hames and D. Rickwood, eds., IRL Press, Washington, DC (1989), pp. 219-228.
B. Zehr et al., "A One-Step, Low Background Coomassie Staining Procedure for Polyacrylamide Gels", Anal. Biochem 182, 157-159 (1989).
Millipore Corp., "Direct Protein Microsequencing", Immobilon Tech Protocol (1987).
M. Hynkapiller et al., "Isolation of Microgram Quantities of Proteins from Poly-acrylamide Gels for Amino Acid Sequence Analysis", Meth. Enzymol. 91, 227-236 (1983).
C. Wilson "Staining of Proteins on Gels: Comparisons of Dyes and Procedures", Meth. Enzymol. 91, 236-247 (1983).

*Primary Examiner*—Jill A. Johnston
*Assistant Examiner*—Maureen M. Wallenhorst
*Attorney, Agent, or Firm*—Foley & Lardner

[57] ABSTRACT

The present invention provides novel dyes for staining proteins, particularly those in electrophoretic gels. The dyes of the invention are derivatives of Coomassie ® dyes. The invention also provides quantitative and qualitative methods for detecting proteins by staining the proteins with a dye of the invention.

12 Claims, No Drawings

PROTEIN STAINING COMPOSITIONS AND METHODS

This is a divisional of application Ser. No. 615,078, filed Nov. 19, 1990, now U.S. Pat. No. 5,132,439, issued Jul. 21, 1992.

BACKGROUND OF THE INVENTION

1. Field of the Invention

The present invention relates to the detection of proteins using synthetic dyes. More specifically, it relates to novel dyes and novel, improved methods of using the dyes for the detection and quantitation of proteins, particularly during electrophoretic separations.

2. Description of the Prior Art

The most powerful and widely used method for the analysis of proteins is the separation of proteins in inert supports by the application of an electric field across the support which causes the proteins in the sample to migrate in a predictable and reproducible manner. See, e.g., Gel Electrophoresis of Proteins: A Practical Approach edited by Hames, B. and Rickwood, D., IRL Press, Washington D.C. (1989). In general, the supports are made from polymers such as polyacrylamide—a polymer of acrylamide and bisacrylamide—or agarose—a polymer of glucose units. Commonly, the separation of the protein sample is performed without the advantage of visualizing the separate components as they fractionate and then, after the separation, the components are detected by staining the constituents by the use of colored dyes. Such dyes include amido black and Coomassie ® dyes, such as Coomassie Brilliant Blue G-250 ® dye (Color Index No. 42655) (referred to hereinafter as Coomassie Blue G-250) or Coomassie Brilliant Blue R-250 ® dye (Color Index No. 42660) (referred to hereinafter as Coomassie Blue R-250). Such staining agents are needed to detect the proteins, for almost all proteins are transparent in solution, polyacrylamide or agarose gels, or other inert supports and thus cannot be detected visually. The staining of the proteins is normally accomplished by soaking the support containing the separated sample in a solution of the stain, which impregnates the support completely, followed by the removal of the stain from the regions of the support not containing protein by such means as passive diffusion or electrophoresis. The maximal sensitivity for detection of any protein depends on the affinity of the dye for the protein and the extinction coefficient of the dye-protein complex. However, the smallest detectable levels of protein in an inert support, such as a polyacrylamide or agarose gel, is usually determined after the level of dye in the regions of the support not containing protein is reduced to the lowest possible level, thus allowing the largest visual difference between the stained protein and the support.

By far, the most widely used and accepted variants of the electrophoretic fractionation methods described above are separations of sodium dodecyl sulfate (SDS)-coated proteins in a support of polyacrylamide or agarose. Such methodology has been widely used to, among other things, determine the purity of protein samples; monitor the reaction of proteins with various agents; separate protein samples or segments of a single protein for subsequent immunological, radiological or protein-sequence analysis; and compare the relatedness of proteins by various analytical methods. This separation methodology, usually abbreviated SDS-PAGE when polyacrylamide gel electrophoresis has been used, has also been employed for the isolation of small amounts of pure protein for various end uses, such as diagnostic or therapeutic applications. Detection of the separated proteins on a SDS-PAGE or SDS-agarose gel is commonly done by exposing the gel, and concomitantly staining the protein bands, with a dye, such as a Coomassie Blue dye, as indicated above. In fact, Coomassie Blue dyes, which are also known by other names such as Serva Blue, Brilliant Blue, Cyanin, Indocyanin, and Eriosin Brilliant Cyanin, as well as others, are most commonly used due to their ease of use and great sensitivity in the detection of very small amounts of protein. See Wilson, C., Meth. Enzymol. 91, 236–247 (1983).

Practitioners in the art have combined the resolving power of SDS-PAGE and SDS-agarose gel electrophoresis with other techniques, such as isoelectric focusing of proteins in various inert supports, to provide some powerful fractionation techniques. These techniques, usually referred to as two-dimensional gel electrophoresis (2-D gel electrophoresis) techniques, are normally performed by a first fractionation of the sample on a polyacrylamide or agarose support by virtue of the intrinsic charges on the proteins followed by second fractionation of the separated polypeptide chains in a direction perpendicular to the direction of the first fractionation after coating of the protein sample with SDS. Hames, B. and Rickwood, D. supra. Such techniques are claimed to be capable of separating 5,000 to 10,000 protein components simultaneously, thus making them the most powerful separation methods available. Again, detection of the proteins in the fractionated sample is done by staining of the support after the fractionations by a stain such as Coomassie Blue dye.

In certain procedures, care is taken to preserve the intrinsic enzymatic and structural properties of the protein components in the sample while performing PAGE or agarose gel electrophoresis. Such gels, known as native gels, then allow the detection of some of the separated proteins by virtue of their activities (e.g., enzymatic activities).

The amounts of the individual protein constituents present in samples fractionated on SDS-PAGE gels can be determined by measurement of the amount of dye bound to the protein bands by densitometry or, following elution of the bound dye, by direct absorption methods.

However, as powerful as the techniques like those described above are, there are several disadvantages inherent in them that limit their use.

While various staining agents such as Coomassie Blue dyes can be used to stain proteins in SDS-PAGE and native-PAGE gels, the staining process takes considerable time, exposes the sample to undesirable conditions (such as acidic pH or the presence of organic solvents), and has been reported to entrap, "fix", proteins in the support. Zehr, B. et al., "A One-step, Low Background Coomassie Staining Procedure for Polyacrylamide Gels," Analyt. Biochem., 182: 157–159(1989); Wilson, C.,"Staining of Proteins on Gels: Comparisons of Dyes and Procedures," Methods in Enzymology, supra. Some researchers have tried to circumvent these difficulties by adding the stain to the separation matrix prior to the separation; however such procedures result in stain levels present in the support matrix that make detection of low levels of protein impossible due to the color they give the support. Schragger et al., Anal. Biochem. 173, 201–205 (1988). Other scientists have used other chemical reagents such as ones that allow the detection of lipoproteins in gel supports. However, these methods do not render detectable the majority of proteins and thus are of very limited use. What is needed, then, are general stains (i.e., dyes) that can be used to provide detectability to all or almost all of the protein in a support without deeply coloring the support.

While some protein components can be identified in native gels, many proteins cannot be easily detected in this way because presence of the protein in a support matrix complicates or prevents detection via structural, enzymatic or other attributes of proteins. Again, what is needed is to improve such methods are dyes that can be used to provide detectability to a protein in such a matrix without relying on the protein's intrinsic structural or enzymatic properties or other intrinsic characteristics that could provide detectability.

While protein can be quantified in gels with great sensitivity by the use of densitometry and related methods, these procedures require that the dye in the gel matrix be substantially completely removed from the areas of the gel not containing protein. This can take a very long time under some circumstances or can require the use of expensive electrical destaining equipment made for this purpose. What is needed are dyes that can be used to quickly and sensitively detect protein in gel supports yet be rapidly removed, or not require removal at all, from the regions of the support not containing protein.

Finally, another drawback with some dyes, including unmodified Coomassie Blue dyes, is the need for very acidic conditions when the dye is used to quantitate protein in solution. Grossberg et al., U.S. Pat. No. 4,219,337; Bradford et al., U.S. Pat. No. 4,023,933. Because some proteins are insoluble under such conditions, they would not be capable of being measured accurately by such methods. Thus, dyes that can be used to quantitate protein under milder pH conditions would be advantageous.

With reference to Coomassie Blue dyes and derivatives thereof, see also Lillie, Conn's Biological Stains, 9th Ed., Williams & Wilkins Co., Baltimore, Md., USA (1977) and Fleming, U.S. Pat. No. 4,966,854.

The aforementioned needs in the art for improved dyes for staining proteins, particularly in applications involving electrophoretic or other separations of proteins through inert supports, are addressed by the present invention. The invention also provides novel and improved methods for detecting proteins.

SUMMARY OF THE INVENTION

The present invention relates to a dye having Formula I:

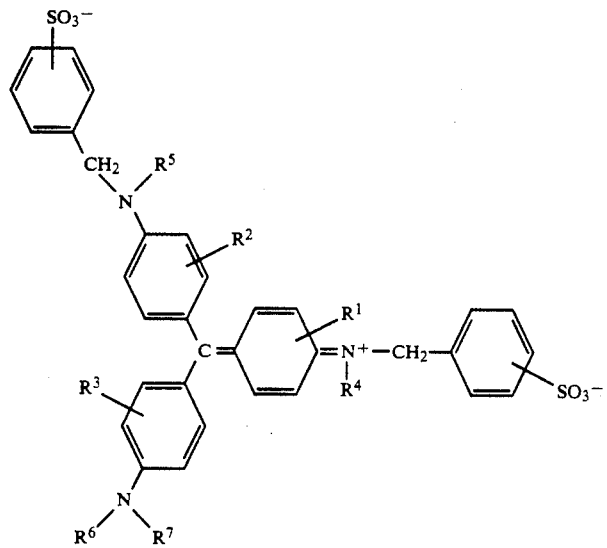

or a salt thereof, wherein $R^1$, $R^2$, and $R^3$ are independently selected from the group consisting of hydrogen, alkyl and aryl groups; $R^4$ and $R^5$ are independently selected from the group consisting of alkyl and aryl groups; $R^6$ is selected from the group consisting of hydrogen, substituted and unsubstituted alkyl, substituted and unsubstituted aryl, and substituted and unsubstituted arylalkyl groups; and $R^7$ a group which renders a Coomassie Blue dye more hydrophobic and is an acyl group of Formula II $$-(C=O)R^8 \qquad \text{II}$$

wherein $R^8$ is selected from the group consisting of substituted and unsubstituted alkyl, substituted and unsubstituted aryl, and substituted and unsubstituted arylalkyl groups.

The invention further relates to a method of detecting a protein which comprises reacting the protein with a dye of Formula I to make a visibly colored complex of the protein with the dye and detecting the complex by observing the color thereof. This method of the invention is especially useful in detecting proteins separated in an solid-support, such as a gel, by a process such as electrophoresis. A particularly advantageous embodiment of the method comprises exposing such a support including a dye-protein complex formed in accordance with the method to an acidic aqueous solution, whereby the contrast between dye-protein complex and the support is intensified.

The invention further relates to a method of detecting protein in a sample comprising the steps of:
(a) applying a sample solution comprising a protein to a solid support;

(b) separating the sample into protein fractions using electrophoresis;
(c) staining the protein on the support with a dye of Formula I; and
(d) detecting the stained protein.

In this method, the dye may be applied to the solid support prior to or during the separation/fractionation process, so that staining occurs simultaneously with the separation/fractionation. Further, the staining may be followed by exposure of the solid support to an acidic aqueous solution to intensify the contrast between dye-protein complexes (i.e., the stained protein) and the support.

The detection methods of the invention may also comprise quantitation of one or more proteins in a protein sample.

DETAILED DESCRIPTION OF THE INVENTION

The present invention is directed to novel dyes and novel methods of using such dyes in the detection and quantitation of proteins.

It has been discovered, surprisingly, that certain organic dyes may be modified in such a way so as to advantageously alter the interaction of the dye with a protein. The modified dye is preferably one of the class known as triphenylmethane dyes, more specifically of the class known as rosaniline dyes.

Preferably, the triphenylmethane dyes of the present invention are modified Coomassie dyes. Thus, the present invention relates to dyes, which are derivatives of Coomassie dyes.

Like Coomassie dyes, the dyes of the invention stain proteins—that is, form dye-protein complexes which are colored and, as such, can be detected visually (with the naked eye) or spectrophotometrically (using a spectrophotometric device).

The dyes of the invention have a number of unexpected advantages over Coomassie dyes in staining proteins and, on account of their improved properties, provide a number of novel and improved methods for detecting and quantitating proteins, especially proteins in solution or separated or fractionated from a sample of proteins during a process such as electrophoresis. Thus, for example, the dyes of the invention allow proteins during electrophoresis to be detected, by visualization, with significantly improved sensitivity because the dyes have improved affinity for proteins and leave the support essentially colorless; permit the sensitive detection and quantitation of proteins by rapid color-enhancement and destaining methods, that, in turn, for example, can be used to quickly prepare a sample of protein for other methods of protein quantification; provide detectability to proteins by making them visible in native gels and thereby obviate the need to rely on structural, enzymatic or other intrinsic properties of proteins to make them detectable in such gels; and permit sensitive quantitation of proteins in solution at pH's between about 3.5 and about 10.5, significantly milder than the very low pH's required for such purposes with unmodified Coomassie dyes.

By the term "Coomassie dye" herein is meant a dye of Formula III

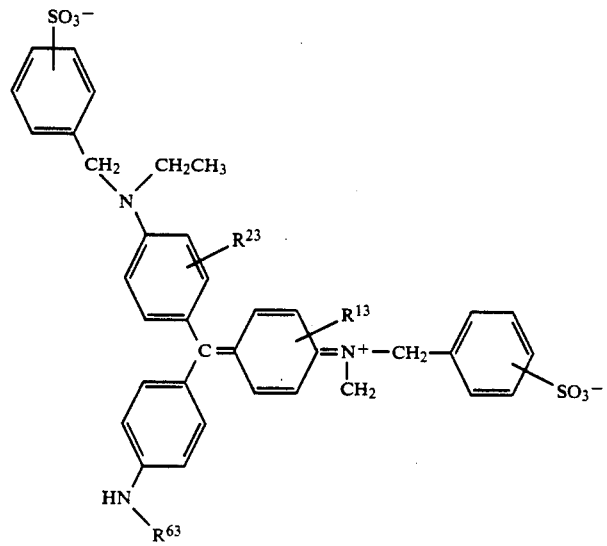

or a salt thereof, wherein $R^{13}$ and $R^{23}$ are independently hydrogen or methyl; and $R^{63}$ is phenyl or ethoxyphenyl. The Coomassie dyes most widely used in the art are Coomassie Brilliant Blue G-250, also referred to as "Coomassie Blue G," which is the dye of Formula III wherein $R^{13}$ and $R^{23}$ are methyl and $R^{63}$ is ethoxyphenyl; and Coomassie Brilliant Blue R-250, also referred to as "Coomassie Blue R," which is the dye of Formula III wherein $R_j$— and $R^{23}$ are hydrogen and $R^{63}$ is ethoxyphenyl. The most commonly employed salt of the Coomassie dyes is the sodium salt.

Thus, the present invention encompasses dyes of Formula I, supra, or salts thereof.

In the more preferred dyes of the invention, $R^1$, $R^2$, and $R^3$ are independently selected from the group consisting of hydrogen and alkyl of 1-6 carbon atoms; $R^4$ and $R^5$ are independently selected from the group consisting of alkyl of 1-6 carbon atoms; $R^6$ is selected from the group consisting of alkyl of 1-20 carbon atoms, phenyl, alkoxyphenyl, wherein the alkyl group is of 1-10 carbon atoms, and alkylphenyl, wherein the alkyl group is of 1-10 carbon atoms; and $R^7$ is a group of Formula IV $$-(C=O)R^{84} \qquad \text{IV}$$

wherein R$^{84}$ is selected from the group consisting of alkyl of 1-20 carbon atoms, phenyl, benzyl, phenyl substituted at any one position with alkyl of 1-10 carbon atoms, chloro, bromo, nitro, or cyano, and benzyl substituted at any one position on the phenyl ring with alkyl of 1-10 carbon atoms, chloro, bromo, nitro or cyano.

In still more preferred dyes of the invention, R$^1$ and R$^2$ are both hydrogen or both methyl; R$^3$ is hydrogen; R$^4$ and R$^5$ are both ethyl; R$^6$ is ethyl or ethoxyphenyl; and R$^7$ is of Formula V

$$(C=O)R^{85} \qquad V$$

wherein R$^{85}$ is selected from the group consisting of alkyl of 1-20 carbon atoms and phenyl. Still more preferred are the dyes wherein R$^1$ and R$^2$ are both hydrogen or both methyl; R$^3$ is hydrogen; R$^4$ and R$^5$ are both ethyl; R$^6$ is ethoxyphenyl; and R$^7$ is of Formula VI

$$-(C=O)R^{86} \qquad VI$$

wherein R$^{86}$ is selected from the group consisting of alkyl of 2-10 carbon atoms and phenyl.

The dye of Formula I wherein R$^1$, R$^2$ and R$^3$ are all hydrogen; R$^4$ and R$^5$ are both ethyl; R$^6$ is ethoxyphenyl; and R$^7$ is octanoyl is called "Promega Green 1." The dye of Formula I wherein R$^1$, R$^2$ and R$^3$ are all hydrogen; R$^4$ and R$^5$ are both ethyl; R$^6$ is ethoxyphenyl; and R$^7$ is acetyl is called "Promega Green 2." The dye of Formula I wherein R$^1$, R$^2$ and R$^3$ are all hydrogen; R$^4$ and R$^5$ are both ethyl; R$^6$ is ethoxyphenyl; and R$^7$ is lauroyl is called "Promeqa Green 3."

Reference herein to an "alkyl" group, without further qualification except as to number of carbons, is to a straight-chain, branched-chain, or cyclic alkyl group, that may be substituted with alkyl groups.

A dye of Formula I is readily synthesized by the skilled beginning with, as starting material, the corresponding compound, which has the same substituents, R$^1$, R$^2$, R$^3$, R$^4$, R$^5$ and R$^6$, as the dye of Formula I that is to be made but has, in place of substituent R$^7$ in said dye, hydrogen. These starting materials, which are, or are simple derivatives of, triphenylmethane dyes, for which methods of synthesis are well known, are readily prepared by the skilled; indeed many of them, such as Coomassie Blue R and Coomassie Blue G, are commercially available.

To prepare a dye of Formula I, the corresponding compound is treated with the corresponding acylating agent, such as the corresponding acylchloride or anhydride, using methods well known to the skilled organic chemist, and the resulting amide (the dye of Formula I) or a salt thereof is isolated. A preferred solvent for the acylation reaction is pyridine.

The present invention also encompasses salts of the dyes of the invention. Salts within the scope of the invention include the salts with sodium, potassium, magnesium, calcium, ammonium, mono-, di-, tri- or tetra-alkyl-substituted ammonium or the like. Sodium is preferred. The salts are preferably "electrophoretically acceptable salts," by which is meant that the cation of the salt will interact with the dye only non-covalently and will migrate in an electric field through an electrophoretic solid support used to separate proteins much more rapidly than protein. Preparation of salts of the dyes of the invention is straightforward for the skilled chemist, entailing simply combining a solution of the dye with a base or a salt, in which the cation is the cation intended for the salt with the dye, under conditions which cause precipitation from the solution of the salt of the cation with the dye. If desired, further steps, well known to the skilled, to isolate and purify the precipitated salt can be taken.

The R$^7$ group increases the hydrophobicity of a dye of the invention in comparison with the corresponding compound with hydrogen in place of R$^7$. As will become apparent from the description below, the R$^7$ group functions to enhance (relative to the corresponding compound with hydrogen in place of R$^7$) the ability of the dye of the invention to stain protein preferentially to staining the gel or solid support comprising the protein. Presumably the R$^7$ group enhances (relative to the corresponding compound with hydrogen in place of R$^7$) the affinity of a dye of the invention for protein while at the same time not affecting or perhaps even decreasing (again, relative to the corresponding compound with hydrogen in place of R$^7$) the affinity of the dye for the gel or solid support.

The method of the invention involves the use of the above described dyes to detect proteins wherein the complex of the dye with the protein is colored and, consequently, renders the protein detectable by visualization or spectrophotometrically. More specifically, the invention involves the use of the above described dyes for detecting protein in solution or using routine electrophoretic techniques well known to artisans in the field of the invention. Hames, B. and Rickwood, D., supra.

The term "protein" is meant to include any protein-like substance, including polypeptides, peptides, radioactive and non-radioactive labeled proteins, glycoproteins, lipoproteins, protein components or subunits, fragments resulting from partial proteolysis of a protein or mixtures thereof, or the like, to which at least one molecule of dye in accordance with the invention is capable of complexing. In electrophoretic applications, the "protein" will typically and preferably have a molecular weight of at least about 1000 daltons.

The dye or a salt thereof, may be dissolved in a water:methanol, or other aqueous or organic, solvent to prepare a "dye reagent."

According to the broad invention, proteins in a sample, which could be a sample of a fluid, such as blood or blood serum, lymph, ascites fluid, urine, microorganism or tissue culture medium, cell extract, or the like derived from a biological source, or a solution thought to include chemically synthesized protein, or an extract or solution prepared from such a fluid from a biological source or solution thought to contain synthesized protein, is applied to a solid support. Preferably, the solid support is a gel, most preferably made either of polyacrylamide or agarose. The protein sample on the solid support is then separated into protein fractions using electophoresis; the solid support may be prepared to include the dye of the invention prior to the electrophoresis or the support with the protein fractions may be stained after the electrophoresis with a dye of the present invention; in either case, the solid support may be destained so that only the protein fractions retain substantial color due to the dye; and, the stained proteins are detected qualitatively and/or quantitatively, on the basis of the color imparted to them by the dye with which they are complexed. Qualitative detection may involve visualization of the solid support directly or of a photograph of the solid support; quantitation may be accomplished using spectrophotometry, densitometry or any other technique known to artisans in the field of protein electrophoresis. The preferred electrophoresis method of the invention uses sodium dodecyl sulfate in a polyacrylamide support (SDS-PAGE). Such method is commonly known to those skilled in the field of the invention. Hames, B. and Rickwood, D. supra and Wilson, C. supra. However, the present invention may also be practiced using native-gels, including polyacrylamide gels, wherein intrinsic properties of the proteins, such as three-dimensional structure and enzymatic activity, are retained.

An aspect of the method of the present invention is that the protein fractions advantageously may be visualized during the electrophoresis process, as described in Examples 5, 7 and 9, below. This feature of the invention is attributable to the fact that the gel remains essentially colorless while the dye of the invention stains the separating protein fractions.

Another aspect of the method of the invention relates to the advantageous rapidity which proteins may be detected. For instance, smaller amounts of protein than can be visualized as the gel is running (as described in Examples 5, 7 and 9) can be visualized in only 1-2 minutes, as described in Examples 6, 8 and 10. Still smaller amounts of protein can be visualized employing the only slightly longer protocol described in Example 12.

A further aspect of the method of the invention relates to the advantageously high sensitivity with which the dyes of the invention permit protein to be detected. For instance, the protocols described in Examples 14 and 15 permit the highly sensitive quantitation of protein in solution and SDS-PAGE, respectively.

The method of the present invention may also include the recovery of the stained protein from the solid support for further analysis. Generally, recovery is accomplished by excising gel with stained bands of proteins from the rest of the gel and subjecting the excised part to further processing according to methods which are well known in the art of the invention. With the dyes of the present invention, the time-consuming detection protocols that are currently employed in the art to identify the location of a protein band in a solid support can be avoided. Further, the protocols currently employed in the art require very careful handling of a solid support to avoid undesirable or unacceptable chemical alteration of the desired protein to be recovered from the support; see, e.g., Lujan et al., Meth. Enzymol. 91, 227-236 (1983). The methods made possible by the dyes of the present invention significantly simplify and reduce the risk of damage to the sought protein during recovery of the protein from a solid support. In addition, with a protocol as described in Example 19, the dyes of the invention provide a rapid method to detect desired protein to facilitate further analysis; this avoids the time-consuming procedures usually required for such methods, see Hames, Chapter 6, in Hames and Rickwood, supra.

Because the dye of the present invention permits one to visualize the stained fraction during electrophoresis, it is possible to remove the protein band of interest by observing its location on the gel, creating a liquid reservoir adjacent to the protein band and running the electrophoresis so that the protein band is captured into the reservoir. The details of this advantageous procedure are found in Example 18.

It has been found, surprisingly, with electrophoretically separated proteins stained with dyes of the invention in solid supports, that suspension of the supports in an acidic aqueous solution (e.g., 5% acetic acid) rapidly and significantly increases the contrast between stained protein and support. This method of enhancing the visibility of protein bands by suspending or exposing the support to an acidic solution (i.e., pH less than about 3) greatly facilitates identification of protein bands in a support and quantification of protein in such bands. See Examples 6, 8, 10 and 12.

The invention further provides a method for sensitively quantitating protein in solution which comprises complexing a dye of the invention with the protein in a solution at a pH between about 3.5 and about 10.5, measuring the optical density of the resulting solution, and comparing the optical density with those from standard solutions of known concentrations of protein. With Coomassie dyes available in the art, very low solution pH's, that were often damaging to protein being analyzed, were required for such analyses of proteins in solution. The method of the invention, of quantitating protein in solution, may be useful, for example, in various diagnostic, including medical diagnostic, applications where the concentration of a particular protein in a body fluid is of significance. The method can be applied to a particular, pre-selected protein, that might, for example, have been eluted into solution from a band, identified with a dye of the invention, on a solid support through which a sample of protein (e.g., a sample of a body fluid) had been electrophoresed. See Examples 13 and 14.

The following examples are illustrative of the invention but are not intended to limit the scope of the invention.

EXAMPLE 1

Synthesis of Promega Green 1

Coomassie Blue R (Aldrich Chemical Co., Milwaukee, Wis., USA, Catalog No. 20,140-5) (10 g, 0.012 moles) was co-evaporated with pyridine (100 ml) to remove moisture. The residue was dissolved in pyridine (100 ml) and the solution was heated to reflux. After 5 min at reflux, octanoyl chloride (10 ml, 0.059 moles) was added and heating was continued for an additional 15 min. The reaction was followed by thin-layer chromatography (TLC) with 3:1 chloroform:methanol as eluent. TLC indicated conversion to a faster migrating product. The reaction was allowed to cool to room temperature, water (1 ml) was added, and the solution was evaporated to dryness.

The residue was dissolved in 3:1 methanol:water (400 ml) and extracted twice with hexane (2×200 ml). The first hexane extract was back extracted with 3:1 methanol:water (50 ml). The methanol:water solutions were pooled to produce the solution of Promega Green 1.

EXAMPLE 2

Synthesis of Promega Green 2

Coomassie Blue R (Aldrich, 20,140-5) (10 g, 0.012 mole) was co-evaporated with pyridine to remove moisture. The residue was dissolved in pyridine (50 ml) and the solution was heated to reflux. Acetic anhydride (5 ml, 0.053 mole) was added and reflux was continued for an additional 15 min.

The reaction was followed by TLC with 3:1 chloroform:methanol as eluent. TLC indicated conversion to a slightly faster migrating product. The reaction was allowed to cool to room temperature and the solution was evaporated to dryness. The residue was redissolved in 1:1 methanol:water (100 ml) and re-evaporated.

The residue was re-dissolved in 1:1 methanol:water (600 ml) and extracted twice with hexane (2×300 ml). The first hexane extract was back extracted with 1:1 methanol:water (100 ml). The methanol:water solutions were pooled to produce the solution of Promega Green 2.

EXAMPLE 3

Synthesis of Promega Green 3

Coomassie Blue R (Aldrich Chemical Co., Milwaukee, Wis., USA, Catalog No. 20,140-5) (10 g, 0.012 moles) was dissolved in pyridine (50 ml) and the mixture was heated to reflux. Lauroyl chloride was added several times over a two-hour interval until a total of 27 ml (0.117 mole) was added.

The reaction was followed by thin-layer chromatography (TLC) with 3:1 chloroform:methanol as eluent. TLC indicated conversion of the blue starting material to a green derivative with little change in mobility. The reaction was allowed to cool to room temperature and the solution was evaporated to dryness.

The residue was dissolved in 2:1 methanol:water (700 ml) and extracted twice with hexane (2×300 ml). The first hexane extract was back extracted with 2:1 methanol:water. The methanol:water solutions were pooled to produce the solution of Promega Green 3.

EXAMPLE 4

Spectral Analysis of Coomassie Blue R and Promega Green 1, 2, 3

A 12 $\mu$g/ml solution of Coomassie Blue R and the three solutions of Promega Green 1, 2, and 3 were diluted approximately 500 fold into a 1:1 solution of methanol:water. The spectra of the resulting solutions were recorded from 700 to 340 nm versus 1:1 methanol:water. This analysis showed that the solution of Coomassie Blue R showed one major absorbing peak in this region of the spectrum with a maximal absorbance of around 590 nm. All of the derivatives gave essentially identical spectra; however, the maximal absorbance of the diluted Promega Green 1 was about twice that seen for the other derivatives. The derivatives had two peak absorptions in the region of the spectrum scanned, a major peak at around 630 nm and a second peak at around 440 nm. The spectral (and chromatographic) differences reported here confirm that the original dye had indeed been derivatized. It is possible that the differences in absorption reflect the variations in the final volume of the derivative solutions and not differences in the absolute absorptivity of the derivatives.

EXAMPLE 5

The Use of Promega Green 1 in the Detection of Proteins During SDS-PAGE Electrophoresis Since earlier reports (Schagger, H. et al., supra.) suggested that reduced levels of SDS in the gel components used in SDS-PAGE electrophoresis would improve staining by related dyes, polyacrylamide gels and buffer used to perform this analysis had reduced SDS concentrations.

Solutions for the formation and electrophoresis of proteins were made according to the instructions given in Experiments in Gene Fusions, Silhavy, Berman, Enquist Cold Spring Harbor Press with the following changes:

a) The SDS concentration in the upper and lower gel buffer components were reduced to result in a 0.05% final SDS concentration in the gel.
b) The SDS concentration in the electrophoretic (electrode) buffer was reduced to 0.04% final concentration.
c) The SDS concentration in the 2× sample buffer was reduced to 1% final concentration.
d) Electrophoresis was performed using a BIO-RAD miniprotein II electrophoresis apparatus and gels were poured such that 1 cm of space was present between the bottom of the loading wells and the separating gel.

The samples used were Promega Mid-Range Molecular Weight Markers (Promega Corp., Madison, Wis., USA) diluted into Sample Buffer to a 1× concentration. The dilutions performed resulted in solutions containing 4, 2, 1.5, 1.0, and 0.5 $\mu$l of Markers per 20 $\mu$l of solution, thus giving protein concentrations of 2, 1, 0.75, 0.5, and 0.25 $\mu$g of each marker band per 20 $\mu$l of solution. The samples were heated to 95° C. for 10 minutes with occasional vortex treatment in 1.5 ml Eppendorf centrifuge tubes and then centrifuged in an Eppendorf centrifuge for 20 seconds to ensure that the sample was denatured and well mixed.

Three 10% SDS-PAGE gels were poured as described in the reference above using the alternate solutions above.

After polymerization of the stacking gel, the gel combs used to form the sample wells in the gel were removed and unpolymerized solution in the wells was rinsed from the loading wells with distilled water. The wells were emptied by inversion of the gel and 20 $\mu$l of the samples described above were loaded into 5 consecutive dried sample wells in each gel. The Promega Green 1 stock described above was diluted into electrode buffer (0.04% SDS w/v final concentration) at a ratio of 0.2, 0.4, and 0.6 ml of dye per 150 ml of electrode buffer. One of these solutions was used to complete the filling of the sample wells in one gel and then the remaining solution was used to fill the cathode buffer chamber used to run the corresponding gel. The loaded gel was inserted into the electrophoretic apparatus. The cathode chamber was filled with the appropriate solutions described above. The anode chambers were loaded with electrode buffer lacking dye and electrophoresis was performed at 160 V until a dark dye band which formed during the separation and moved towards the anode began to emerge from the bottom of the gel, this took approximately 1 hour.

A white plastic card was placed behind the gel to allow visualization of the gel without interference from the color in the cathode chamber. During electrophoresis, the protein bands in the lanes containing 2.0 and 1.0 $\mu$g of protein per band became visible during the separation and by the end of the run, most of the bands in the lanes containing 0.75 and 0.5 $\mu$g of protein were visible against an essentially clear background. Slightly easier detection of the bands were observed in the gels containing increased levels of dye, however a corresponding increase in the color in the gel background was seen.

EXAMPLE 6

Enhancement of the Staining of Proteins in SDS-PAGE Gels Stained with Promega Green 1

The gels described above were placed in 5% acetic acid following the termination of the electrophoretic separation. Within one to two minutes the gel developed a light green background but the protein bands dramatically darkened to a green color. All of the protein bands in all the lanes having sample were now visible in all the gels. Again, the color of the background darkened to a greater degree when greater concentrations of dye were used.

Upon allowing the gels to incubate overnight in 5% acetic acid, the stain in the background of the gel was released into the solution. The intensity of the color in the protein bands appeared to darken slightly.

EXAMPLE 7

Use of Promega Green 2 in the Detection of Proteins During SDS-PAGE Electrophoresis The ability of Promega Green 2 to stain proteins during electrophoresis was done as described above except that 1.0, 2.0, and 3.0 ml of the solution of Promega Green 2 was added separately to individual cathode buffer solution (150 ml of electrode buffer). Gels were run as before. The lanes containing 2.0 and 1.0 µg protein per band were visible while the gel was running if a white plastic card was placed behind the gel during electrophoresis.

EXAMPLE 8

Enhancement of the Staining of Proteins in SDS-PAGE Gels Stained with Promega Green 2

The gels above were placed in 5% acetic acid following termination of the electrophoretic separation. Within 1-2 minutes, all the gels turned light green and the color of the stained bands intensified such that all proteins were visible—even in the lane containing 0.25 µg protein/band.

After overnight incubation, the stain in the gel diffused into the acetic acid solution, however the protein bands appear to have become slightly faded.

EXAMPLE 9

Use of Promega Green 3 in the Detection of Proteins During SDS-PAGE Electrophoresis The ability of Promega Green 3 to stain proteins during electrophoresis was done as described above except that 0.2, 0.3 and 0.5 ml of the dye solution of Promega Green 3 was added separately to individual cathode buffer solutions (150 ml of electrode buffer). Gels were run as before. The lanes containing 2.0 and 1.0 µg protein per band were visible while the gel was running if a white plastic card was placed behind the gel during electrophoresis.

EXAMPLE 10

Enhancement of the Staining of Proteins in SDS-PAGE Gels Stained with Promega Green 3

The gels above were placed in 5% acetic acid following termination of the electrophoretic separation. Within 1-2 minutes, all the gels turned light green and the color of the stained bands intensified such that all proteins were visible—even in the lanes containing 0.25 µg protein/band.

After overnight incubation, most of the stain in the gel had diffused into the acetic acid solution, however a greater amount of stain remained in the gel than was seen with Promega Green 1, leading to a darker background color.

From these studies, it appeared that Promega Green 1 had the most desirable properties of the compounds tested although all of the derivatives performed well in this enhancement method. The method has not been reported for any other protein dye, including the Coomassie dyes.

EXAMPLE 11

The Use of Promega Green 1 in Polyacrylamide Gels not Containing SDS

A polyacrylamide gel was made containing a 10% separating gel and a 3% stacking gel having 50 mM tris-HCl pH 8.0 as a buffer. A sample loading solution was made containing Promega Green 1 dissolved in 50 mM tris - cc pH 8.0, 20% glycerol. Samples of bovine serum albumin (BSA) and carbonic anhydrase was added to the sample buffer. The samples were loaded onto the gel and the gel was assembled into a BioRad miniprotean II gel system. An electrode buffer solution of 50 mM tris pH 8.0 was used to fill the buffer chamber and a voltage of 150 volts were applied to the apparatus. The BSA and carbonic anhydrase samples were seen to migrate through the gel as stained bands that had bound a fraction of the stain in the sample loading buffer. Therefore, the stain need not be used only in systems containing SDS.

EXAMPLE 12

Development of a Method for the Rapid Enhancement of the Staining of Proteins With Promega Green 1 that Results in Low Residual Color in the Gel As mentioned earlier, it is desirable to be able to quickly visualize proteins in a manner that also results in very little color retention in the gel background so that protein quantitation by methods such as densitometry can be accurately and rapidly performed.

In order to develop such a method, several 10% SDS-PAGE gels made as described in Example 5 were made and loaded with samples made as described therein with the following changes: the sample loading size was reduced to 5 µl; and the solutions were made to contain 1.0, 0.50, 0.25, and 0.125 µg of each protein band of Promega Mid Range Molecular Weight Markers in 5 µl of the sample. Each gel was loaded such that duplicate panels of samples containing the various concentrations of protein were present in 4 consecutive lanes. The gels were run as described above and the gel was cut between the duplicate sample panels. A gel segment containing one panel was placed in each of the following solutions: 30 ml of 2% glacial acetic acid (A); 30 ml of 2% glacial acetic acid in 10% methanol (B); 2% glacial acetic acid in 20% methanol (C); 2% glacial acetic acid in 30% methanol (D); 30 ml of water (E); 30 ml of 10% methanol (F); 30 ml of 20% methanol (G); and 30 ml of 30% methanol (H). The solutions were incubated with the gel segments for 10 minutes at room temperature and gently rotated at 40 rpm to prevent settling of the gel segments in the containers. After this time, the original solutions were removed and the following liquids were applied to the gel segments: 30 ml of 2% acetic acid was applied to the segments treated with A and E; 30 ml of 2% acetic acid in 10% methanol was applied to the segments treated with B and F; 30 ml of 2% acetic acid in 20% methanol was applied to the segments treated with C and G; and 30 ml of 2% acetic acid in 30% methanol was applied to the segments treated with D and H. The segments were then incubated for 60 minutes at room temperature with gentle rotation (40 rpm).

After this time, the segments first treated with solution E, F, G, and H all showed less background staining than their corresponding segments treated with A, B, C, and D. In addition, all protein bands were visible in all gel segments -demonstrating that at least 125 ng of protein can be detected using these procedures. In addition, although the gels were slightly reduced in size, those treated with increasing concentrations of methanol had less background staining regardless of whether the gel segment was first treated with a solution containing acetic acid. In particular, the segment treated with solution set H had very little background staining remaining and could be used to quantitate the protein bands present.

Protocols using other dyes that have been developed for the sensitive detection of protein sometimes employ the incubation of the gel in solutions containing the stain followed by incubation of the gel in solutions lacking the stain. In order to determine if such a protocol could be used to allow even lower levels of protein to be detected using Promega Green 1, the following study was performed.

Three SDS-PAGE gels were constructed as described in Example 5. Samples of Promega Mid-Range Molecular Weight Markers were made and treated as described in that Example with the following changes: the sample sizes applied to the gel were 5 $\mu$l; and individual samples were made to contain 1.0, 0.5, 0.25, 0.125, 0.0625, 0.0312, and 0.0156 $\mu$g of each protein band in the 5 $\mu$l samples. Samples were loaded into the gels and subjected to electrophoresis as described in that section. After electrophoresis, the gels were incubated in 50 ml solutions containing 30, 40 or 50% methanol and a 1:5000 dilution of the Promega Green 1 Stock solution for 10 minutes with gentle agitation. After this time, the liquids were removed and the following solutions were applied to the gels: the gel treated with the 30% methanol solution above was treated with 50 ml of 30% methanol, 2% acetic acid containing a 1:10,000 dilution of Promega Green 1; the gel treated with the 40% methanol solution was treated with 50 ml of 40% methanol, 2% acetic acid containing a 1:10,000 dilution of Promega Green 1, and: the segment treated with the 50% methanol solution was treated with 50 ml of 50% methanol, 2% acetic acid containing a 1:10,000 dilution of Promega Green 1. The gels were then gently rotated at 40 rpm at room temperature for 10 minutes.

After this time, the solutions were removed and 50 ml solutions corresponding to that removed, but lacking the dye, were applied and the gels were gently rotated at 40 rpm at room temperature for 10 minutes. After 60 minutes, all the gels showed very little background staining and all the bands of protein in the lane containing 62.5 ng of protein per band was visible. This protocol then can be used to detect very small amounts of protein with little background staining.

EXAMPLE 13

The Effect of Solution pH on the Absorption of Promega Green 1 in the Presence and Absence of Protein The effect of solution pH on the absorption of Promega Green 1 in the presence and absence of added protein was studied by dilution of Promega Green 1 solution at a ratio of 1:1000 (v/v) into various solutions containing 0 or 100 $\mu$g of protein (bovine serum albumin (BSA)) per ml of liquid. The solutions tested were highly acidic (1N HCl), moderately acidic (2% acetic acid), weakly acidic (50 mM ammonium acetate pH 4.0), weakly basic (50 mM ammonium bicarbonate pH 7.8), and strongly basic (500 mM tris base). The absorption spectra of the solutions were measured from 700 to 340 nM and the peak absorbances are reported below.

| solution | Protein Absent | | Protein Present | |
|---|---|---|---|---|
| | max | ABS | max | ABS |
| strongly acidic | 649 nm | 0.27 | 641 nm | 0.39 |
| moderately acidic | 631 nm | 0.83 | 635 nm | 0.98 |
| weakly acidic | 636 nm | 0.49 | 638 nm | 0.25 |
| weakly basic | 636 nm | 0.49 | 637 nm | 0.26 |
| strongly basic | 637 nm | 0.22 | 637 nm | 0.128 |

These results show that the absorbance of the dye in the absence of protein displays a dependence on the pH of the solution, indicating that the dye can be used as a wide range pH indicator.

In addition, the dye protein complex displays a different absorption than the dye alone. The effect can result either in an increased level of absorption as is shown in strongly acidic solutions, or a decrease in absorption as is shown for weakly acidic or basic solutions. Thus the dye can be used in protein quantitation formats that can measure the presence of protein by either measuring an increase or decrease in the dye protein complex compared to the dye itself.

EXAMPLE 14

Development of a Sensitive Solution Protein Quantitation Assay Using Promega Green 1

In order to conclusively determine a format for the sensitive quantitation of protein in solution using Promega Green 1, Promega Green 1 was diluted at a ratios of 1:250 (v/v) and 1:1000 (v/v) into 0.5M tris base containing 0, 5, 10, 20, 40, 60, 80, and 100 $\mu$g protein (BSA) per ml of solution. After incubation of the solutions for 3 hours at room temperature, the absorption of the solutions at 630 nM was measured.

| Protein concentration ($\mu$g/ml) | Absorption at 630 nM Dilution of dye | |
|---|---|---|
| | 1:1000 | 1:250 |
| 0 | 0.079 | 0.543 |
| 5 | 0.069 | 0.515 |
| 10 | 0.059 | 0.472 |
| 20 | 0.051 | 0.427 |
| 40 | 0.048 | 0.386 |
| 60 | 0.047 | 0.358 |
| 80 | 0.044 | 0.342 |
| 100 | 0.043 | 0.317 |

These results show that the above format can be used to determine the protein content of solutions at very sensitive levels.

EXAMPLE 15

The Use of Promega Green 1 for the Quantitation of Proteins Separated by SDS-PAGE Electrophoresis The use of Promega Green 1 for the quantitation of proteins separated using SDS-PAGE electrophoresis was demonstrated in the following way. A 10% SDS-PAGE gel was made as described in the Example 5. Promega Mid-Range Molecular Weight Standards were diluted into loading buffer to produce solutions containing 2.0, 1.0, 0.5, and 0.25 $\mu$g of protein per band in 5 $\mu$l of solution. Duplicate 5 $\mu$l solutions of each of these solutions were loaded into 1 of the 10 sample wells in the gel after the solutions were heated at 95° C. for 10 minutes. The gel was then electrophoresed at 160 V until the running dye just eluted from the bottom of the gel. The gel was enhanced and destained for 90 minutes in 30% methanol, 4% acetic acid.

One of the pair of duplicate bands for the 92, 67, 50 and 45 kilodalton standards from the lanes containing 2.0, 1.0, 0.5, and 0.25 $\mu$g of protein per band were excised with a razor blade as was two control gel segments from regions of the gel not containing protein. The excised segments were placed in individual 1.5 ml Eppendorf tubes containing 2% SDS and allowed to incubate at room temperature for 72 hours. After this time, the solutions were removed from the extracted segments and acetic acid was added to 2% (u/v) final concentration. The absorption of the solutions at 630 Nm was then measured.

| Protein Blank amount region ($\mu$g/band) | Absorbance at 630 Nm Protein Sample | | | |
|---|---|---|---|---|
| | 92 kD | 67 Kd | 50 Kd | 45 Kd |
| 0 0.018, 0.015 | | | | |
| 0.25 | .032 | .052 | .053 | .042 |
| 0.50 | .053 | .074 | .063 | .064 |
| 1.00 | .083 | .138 | .105 | .126 |
| 2.00 | .128 | .192 | .138 | .195 |

These data show that Promega Green 1 can be used to quantitate proteins separated by SDS-PAGE electrophoresis. The method is very sensitive, allowing as little as 250 ng of protein to be measured.

EXAMPLE 16

The Use of Promega Green 1 for the In-Situ Staining of Proteins During Transfer to Immobilizing Supports The use of immobilizing supports such as nitrocellulose, nylon, glass or polyvinyl difluoride has become very common in the immunochemical or sequence analysis of proteins. In order to demonstrate the use of Promega Green 1 for the staining of proteins during the transfer of proteins to such supports, an SDS-PAGE gel was made, loaded and run as described in Example 15. A segment of Immobilon P TM from Millipore Company was wetted in 100% methanol for 30 seconds then equilibrated in transfer buffer (25 mM tris base, 192 mM glycine) for two minutes. Two Whatman 3 mM sheets were soaked in transfer buffer and these components were then used to construct a transfer sandwich composed of one sheet of Whatman paper, the SDS-PAGE gel, the Immobilon sheet, and the final sheet of Whatman. The sandwich was placed in a Hoeffer transfer apparatus and oriented in the apparatus such that the Immobilon side of the sandwich was oriented toward the positive electrode. The apparatus was placed at 4° C. and 10 V were applied to the apparatus for 30 minutes then the voltage was increased to 30 V for an additional 120 minutes.

The transfer apparatus was then disassembled and the surface of the Immobilon membrane that had been in contact with the gel displayed visible protein bands in the lanes that had contained 2.0 and 1.0 $\mu$g protein per band. The Immobilon membrane was then soaked in 45% methanol, 5% acetic acid for 2 minutes. This procedure enhanced the staining of the proteins transferred to the Immobilon membrane such that the protein band at all concentrations became easily visible. These data demonstrate that the dye can be used to stain proteins during electrophoretic transfer to immobilizing supports and that the enhancement seen in gels can also be demonstrated with protein transferred to such supports.

EXAMPLE 17

The Use of Promega Green 1 in the Recovery of Proteins Separated by Gel Electrophoresis The Use of Promega Green 1 in the recovery of proteins separated by gel electrophoresis was demonstrated in the following way. An 8% SDS-PAGE gel was prepared as described above and loaded with Promega Mid-Range Molecular Weight Markers at a concentration of 4 $\mu$g of protein per lane. The gel was run at 160 V with 200 $\mu$l of octyl Coomassie in the cathode buffer.

After electrophoresis, the gel segments containing the 92, 67, 50, 45 and 40 kilodalton proteins were excised from four consecutive lanes, minced, and placed in individual 1.5 ml Eppendorf tubes containing 0.5 ml of 50 mM ammonium bicarbonate pH 7.8 containing 0.02% SDS (u/v). The tubes were then incubated at 50° C. for 14 hours.

After that time, the tubes were spun for 1 minute in a Microfuge to pellet the minced acrylamide and 0.47 ml of the supernate was removed to new 1.5 ml tubes. Two of the four solutions from each of the eluted protein samples were dried in a Speed-Vac, the other pair was first ultrafiltered through a 5000 kilodalton cut-off Milligen centrifugal concentrator by centrifugation in a microfuge for 30 minutes. These concentrated solutions were then dried in a Speed Vac.

The dried samples were resuspended in 25 $\mu$l of 1× loading buffer and heated at 95° C. for 10 minutes. These samples were then loaded in two 15 wells, 0.75 mM 10% SDS-PAGE gels made as above. The gels were then run at 160 V with 200 $\mu$l of octyl Coomassie in the cathode buffer. After electrophoresis, the gel was enhanced for 1 hour in 307 methanol, 4% acetic acid. At this time in the gel, the expected protein bands could be seen in the lanes. These data demonstrate that the dye can be used in the recovery of proteins separated by gel electrophoresis.

EXAMPLE 18

The Use of Promega Green 1 for the Recovery of Protein Separated by Gel Electrophoresis Using a Novel Recovery Method Because Promega Green 1 can be used to stain protein during electrophoretic separations, we determined that proteins separated by gel electrophoresis can be recovered into a liquid reservoir placed in the gel. This is possible only with in-situ stained proteins because it would not be obvious where to place the liquid reservoir otherwise.

Accordingly, an 8% SDS-PAGE gel was made, loaded and run as described in the preceding example. After the run was complete, one of the glass plates encasing the gel was removed and 1.0×0.3 cm slots were excised from the gel immediately below the 92, 60, 40, and 31 kilodalton standards. The gel was then placed in a flat bed electrophoresis apparatus which had had its buffer chambers filled with 25 mM tris base, 192 mM glycine (electrode buffer) to the level of the central, raised portion of the apparatus. The gel was placed in the apparatus such that the acrylamide gel above the remaining glass plate was filled with electrode buffer. The slots were also filled with electrode buffer and electric connection was made between the gel and the buffer chambers by use of Whatman 3 mM paper wicks soaked in transfer buffer and then 160 V was applied to the apparatus for 2 minutes. After this, the buffer in the slots was removed and placed in 1.5 ml Eppendorf tubes, the slots were refilled with fresh electrode buffer and the voltage was reapplied. This cycle was repeated 3 more times and the samples from identical slots were pooled and dried in a Speed-Vac.

After drying, the samples were redissolved in 25 µl of 1× sample buffer. A 10% SDS-PAGE gel was made as described in Example 5. The samples were loaded onto the gel and electrophoresis was performed as described in that section. After the run was complete, the staining was enhanced in 30% methanol, 4% acetic acid.

Analysis of the gel showed that the desired protein band had been captured by this method. Thus, this protocol can be used to isolate proteins electrophoretically without the need to: stain the gel following electrophoresis; destain the gel; re-equilibrate with SDS; or electroelute the protein by use of special electrophoresis equipment. This method specifically allows this advantage due to the fact that the separating protein bands are visible during the initial electrophoretic separation.

EXAMPLE 19

The Use of Promega Green 1 in the Analysis of Partial Proteolytic Products of a Protein The comparison of proteins by analysis of the products of partial proteolysis using SDS-PAGE electrophoresis has been reported extensively in the literature. This analysis, termed Cleveland analysis, can provide important information on many different types of covalent changes that can occur on proteins.

To determine if the new dye can be used advantageously in such analysis, the following study was performed.

An 8% SDS-PAGE gel was made as described in Example 5. A 5 µl sample of 1× loading buffer containing 4 µg of Bovine serum albumin previously heated at 95° C. for 5 minutes was placed in several of the wells and electrophoresis was performed as described in the section mentioned above.

A second 1.0 mM thick 16% SDS-PAGE gel was made as described in the section above.

After electrophoresis, segments of the gel containing the BSA sample were excised by use of a razor blade and loaded into three of the sample wells of the second gel. Then, 20 µl of 1× loading buffer containing 0.5 µg of Endoprotease Glu C, 0.5 µg of Endoprotease Lys C and 0.1 µg of Alkaline Protease, respectively, was added to individual wells containing the gel slices. Also, 5 µl of a solution of 4 µg of BSA in 1× loading buffer that was previously heated to 95° C. for 15 minutes was placed in a second set of three wells. To each of these three samples was added individual 20 µl solutions containing 0.5 µg of Endoprotease Glu C, 0.5 µg of Endoprotease Lys C, or 0.1 µg of Alkaline Protease, respectively. The gel was then run at 50 V with 200 µl of octyl Coomassie (i.e., Promega Green 1) present in the cathode buffer. When the dye band reached the interface between the stacking gel and the separating gel, the voltage to the apparatus was shut off for 30 minutes, then the voltage was reapplied, adjusted to 160 V and electrophoresis continued until the tracking dye emerged from the bottom of the gel. At this point, the staining was enhanced using 30% methanol, 4% acetic acid. The partial proteolytic pattern of the digested samples was readily apparent in a very short period of time.

These results indicate that the use of Promega Green 1 does not interfere with Cleveland type protein analysis. In addition, they indicate that the dye simplifies such analysis by eliminating the staining, destaining and re-equilibration steps normally needed to perform such analysis.

It is to be understood that the invention is not limited to the particular embodiments specifically disclosed herein as exemplary, but embraces such modified forms thereof as come within the scope of the following claims.

We claim:

1. A method of detecting a protein in a polyacrylamide or agarose support, in which the protein has been electrophoresed, comprising staining the protein in the support with a dye of Formula X

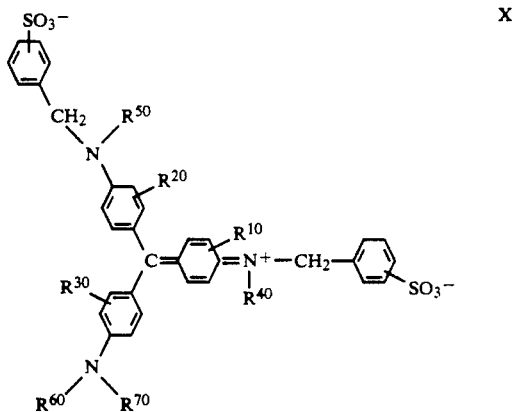

wherein $R^{10}$, $R^{20}$, and $R^{30}$ are independently selected from the group consisting of hydrogen and alkyl of 1–6 carbon atoms; $R^{40}$ and $R^{50}$ are independently selected from the group consisting of alkyl of 1–6 carbon atoms; $R^{60}$ is selected from the group consisting of alkyl of 1–20 carbon atoms, phenyl, alkoxyphenyl, wherein the alkyl group is of 1–10 carbon atoms, and alkylphenyl, wherein the alkyl group is of 1–10 carbon atoms; and $R^{70}$ is a group of Formula XI $$-(C=O)R^{80} \qquad XI$$

wherein $R^{80}$ is selected from the group consisting of alkyl of 1–20 carbon atoms, phenyl, benzyl, phenyl substituted at any one position with alkyl of 1–10 carbon atoms, chloro, bromo, nitro, or cyano, and benzyl substituted at any one position on the phenyl ring with alkyl of 1–10 carbon atoms, chloro, bromo, nitro or cyano, bathing the support in an aqueous solution with a pH less than about 3, and visualizing the stained protein.

2. The method of claim 1 wherein the support is polyacrylamide and, in the dye, $R^{10}$ and $R^{20}$ are both hydrogen or both methyl; $R^{30}$ is hydrogen; $R^{40}$ and $R^{50}$ are ethyl; $R^{60}$ is ethoxyphenyl; and $R^{80}$ is selected from the group consisting of alkyl of 1-11 carbon atoms and phenyl.

3. The method of claim 2 wherein, in the dye, $R^{80}$ is methy, heptyl, or undecyl.

4. The method of claim 2 wherein the aqueous solution is a solution of about 5% acetic acid.

5. The method of claim 3 wherein the aqueous solution is a solution of about 5% acetic acid.

6. A method of detecting a protein which comprises making a visibly colored complex of the protein with a dye of Formula X

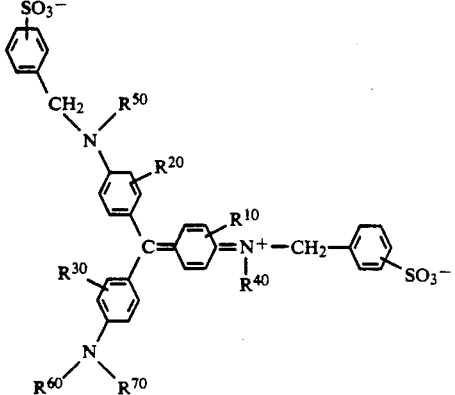

wherein $R^{10}$, $R^{20}$, and $R^{30}$ are independently selected from the group consisting of hydrogen and alkyl of 1-6 carbon atoms; $R^{40}$ and $R^{50}$ are independently selected from the group consisting of alkyl of 1-6 carbon atoms; $R^{60}$ is selected from the group consisting of alkyl of 1-20 carbon atoms, phenyl, alkoxyphenyl, wherein the alkyl group is of 1-10 carbon atoms, and alkylphenyl, wherein the alkyl group is of 1-10 carbon atoms; and $R^{70}$ is a group of Formula XI

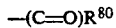

—(C=O)$R^{80}$  XI wherein $R^{80}$ is selected from the group consisting of alkyl of 1-20 carbon atoms, phenyl, benzyl, phenyl substituted at any one position with alkyl of 1-10 carbon atoms, chloro, bromo, nitro, or cyano, and benzyl substituted at any one position on the phenyl ring with alkyl of 1-10 carbon atoms, chloro, bromo, nitro or cyano, and detecting the complex by observing the color thereof.

7. The method of claim 6 wherein the protein is in a polyacrylamide or agarose gel.

8. The method of claim 7 wherein the support is polyacrylamide and, in the dye, $R^{10}$ and $R^{20}$ are both hydrogen or both methyl; $R^{30}$ is hydrogen; $R^{40}$ and $R^{50}$ are ethyl; $R^{60}$ is ethoxyphenyl; and $R^{80}$ is selected from the group consisting of alkyl of 1-11 carbon atoms and phenyl.

9. The method of claim 8 wherein, in the dye, $R^{80}$ is methy, heptyl or undecyl.

10. A method of detecting protein in a sample comprising the steps of:
   (a) applying a sample solution comprising a protein to a polyacrylamide or agarose gel;
   (b) separating the protein of the sample solution into protein fractions using electrophoresis;
   (c) staining the protein on the gel with a dye of Formula X

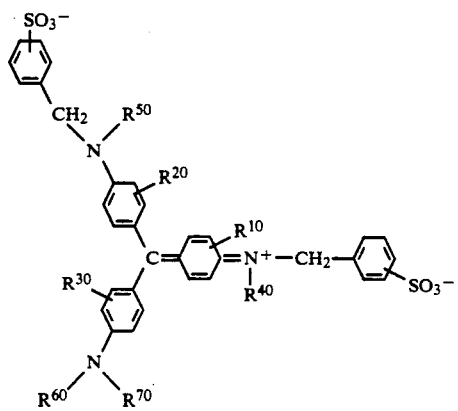

wherein $R^{10}$, $R^{20}$, and $R^{30}$ are independently selected from the group consisting of hydrogen and alkyl of 1-6 carbon atoms; $R^{40}$ and $R^{50}$ are independently selected from the group consisting of alkyl of 1-6 carbon atoms; $R^{60}$ is selected from the group consisting of alkyl of 1-20 carbon atoms, phenyl, alkoxyphenyl, wherein the alkyl group is of 1-10 carbon atoms, and alkylphenyl, wherein the alkyl group is of 1-10 carbon atoms; and $R^{70}$ is a group of Formula XI

—(C=O)$R^{80}$  XI wherein $R^{80}$ is selected from the group consisting of alkyl of 1-20 carbon atoms, phenyl, benzyl, phenyl substituted at any one position with alkyl of 1-10 carbon atoms, chloro, bromo, nitro, or cyano, and benzyl substituted at any one position on the phenyl ring with alkyl of 1-10 carbon atoms, chloro, bromo, nitro or cyano; and
   (d) detecting the stained protein by observing the color thereof.

11. The method of claim 10 wherein the gel is polyacrylamide and, in the dye, $R^{10}$ and $R^{20}$ are both hydrogen or both methyl; $R^{30}$ is hydrogen; $R^{40}$ and $R^{50}$ are ethyl; $R^{60}$ is ethoxyphenyl; and $R^{80}$ is selected from the group consisting of alkyl of 1-11 carbon atoms and phenyl.

12. The method of claim 11 wherein, in the dye, $R^{80}$ is methyl, heptyl or undecyl.

* * * * *